United States Patent [19]

Portner et al.

[11] 4,167,046

[45] Sep. 11, 1979

[54] BLOOD PUMPING DEVICE

[75] Inventors: Peer M. Portner, Berkeley; Jal S. Jassawalla, San Francisco, both of Calif.

[73] Assignee: Andros, Inc., Berkeley, Calif.

[21] Appl. No.: 859,915

[22] Filed: Dec. 12, 1977

[51] Int. Cl.² .......................... A61F 1/24; F04B 17/00
[52] U.S. Cl. ....................................... 3/1.7; 128/1 D; 128/DIG. 3; 417/412; 417/479
[58] Field of Search ............ 128/1 D, DIG. 3; 3/1.7; 417/412, 472, 479

[56] References Cited

U.S. PATENT DOCUMENTS

| | | | |
|---|---|---|---|
| 3,007,416 | 11/1961 | Childs | 417/479 X |
| 3,097,366 | 7/1963 | Winchell | 417/412 X |
| 3,148,624 | 9/1964 | Baldwin | 3/1.7 X |
| 3,579,644 | 5/1971 | Esmond | 3/1.7 |
| 3,949,734 | 4/1976 | Edwards et al. | 128/DIG. 3 |
| 3,963,380 | 6/1976 | Thomas, Jr. et al. | 128/7 D X |
| 4,052,849 | 10/1977 | Dumbaugh | 417/412 X |
| 4,091,471 | 5/1978 | Richter | 128/1 D X |

FOREIGN PATENT DOCUMENTS 92963 12/1968 France ............................................ 3/1.7

OTHER PUBLICATIONS

"Staged Replacement of the Human Heart", Cooley et al., vol. XV, Trans. Amer. Soc. Artif. Int. Organs, 1969, pp. 252–263.
"Booster Pump Gives New Life", Popular Science, 12/65, p. 48.
"Physiological Evaluation of Co-Pulsation", Sato et al., vol. XV, Trans. Amer. Soc. Artif. Int. Organs, 1969, pp. 449–453.

Primary Examiner—E. H. Eickholt
Attorney, Agent, or Firm—Fitch, Even & Tabin

[57] ABSTRACT

A blood pumping device is described for internal use in humans or animals and which is particularly suitable for use as a left ventricular assist device. The device is comprised of a unitary pancake-shaped deformable sac of flexible resilient, blood compatible material. A pair of oppositely acting plates on each side of the pancake-shaped sac are moved toward and away from each other by the action of driving means to deform the sac and provide the pumping action. Inlets and outlets are arranged in the annular side wall of the sac.

8 Claims, 4 Drawing Figures

BLOOD PUMPING DEVICE

This invention relates generally to blood pumping devices for internal use in humans or animals. More particularly, the invention relates to an improved blood pumping device which is particularly suited for use as a left ventricular assist device.

Efforts to develop an artificial heart have produced a wide variety of blood pump configurations. This particular invention relates to the so-called sac type pumps in which a deformable sac is utilized to provide the pumping action. Deformation of the sac to reduce its internal volume causes the expelling of the sac contents or a portion thereof. Return of the sac to its original undeformed condition expands its internal volume and causes inflow of fluid into the sac for the next pumping stroke. These types of pumps are analogous to the action of the heart in humans and animals.

Devices of the aforementioned type may be actuated in a variety of ways. Some devices employ pneumatic actuation. Others employ expanding or contracting fluids. Still others employ electrical devices such as solenoids for actuation.

With any type of blood pump designed to be implanted in an animal or human, however, a number of common problems are presented. First of all, the device must be suitable for implantation in that its size and configuration must be such as to be readily accommodated in some body cavity. Inlet and outlet connections to the device should be such as to facilitate connection of the device into the blood stream to provide the desired pumping action. Coupling of the pump drive to the pump itself must be relatively simple and reliable. The pump must be highly reliable for long periods of time of continuous use. Finally, flow characteristics of the pump should be such as to prevent thrombus formation or clotting in the blood. Other problems which exist in connection with the design of a blood pump are discussed below.

Although prior art blood pump designs have provided promise in certain respects, most have had sufficiently significant defects as to prevent their successful use. Among these defects has been the presence of a diaphragm-housing junction or discontinuity which frequently results in thrombus formation. Other factors contributing to thrombus formation have been poor internal geometry, poor material choice, and wrinkling during deformation of the sac. Many prior art pumps have had the disadvantage of large volume or size in one or more dimensions which made implantation difficult.

It is an object of the present invention to provide an improved blood pumping device for internal use in humans or animals.

Another object of the invention is to provide an improved blood pumping device particularly suitable for use as a left ventricular assist device.

A further object of the invention is to provide an improved blood pumping device of low volume, and which minimizes the likelihood of thrombus formation.

Other objects of the invention will become apparent to those skilled in the art from the following description, taken in connection with the accompanying drawings wherein.

Figure 1:
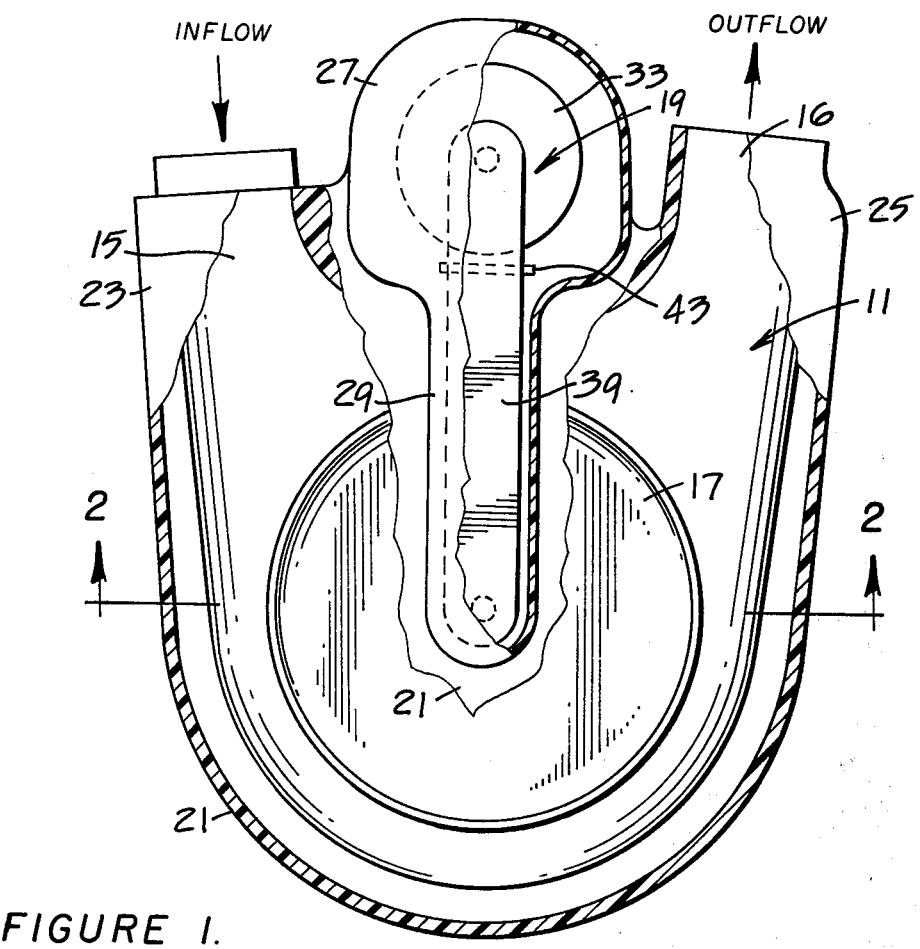
FIG. 1 is a schematic plan view, partially in section, of a blood pumping device constructed in accordance with the invention.

Very generally, the blood pumping device of the invention comprises a deformable sac 11 having, in the non-deformed configuration, a pair of opposite substantially planar walls 12 and 13 of substantially circular shape joined by an annular wall 14 of substantially semi-circular cross-section. The sac is formed in a unitary seamless piece of flexible resilient material having inlet means 15 and outlet means 16. A pair of pusher plates 17 and 18 are disposed on opposite sides of the sac. Each of the pusher plates are engageable with a respective one of the planar walls of the sac for displacing the planar walls toward each other to deform the sac. Means 19 are provided for periodically displacing both of the plates toward each other.

Figure 2:
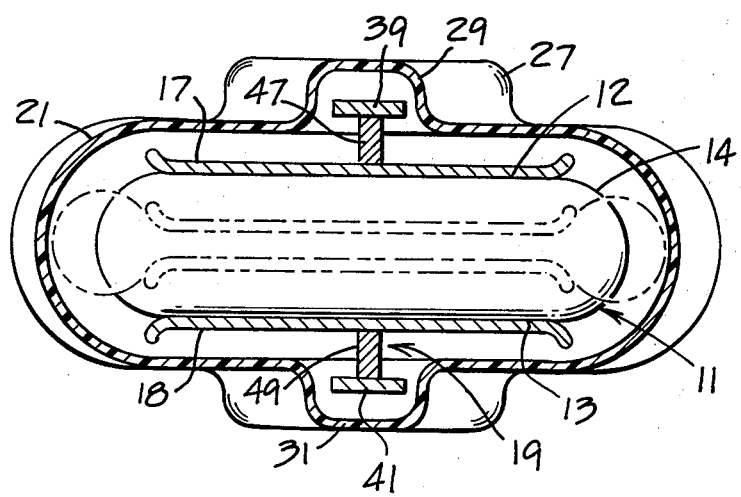
FIG. 2 is a sectional view taken along the line 2—2 of FIG. 1.

Referring now more particularly to FIGS. 1 and 2, the deformable sac 11 may be seen contained within a housing 21 of rigid material formed generally in the same shape as that of the sac. The housing 21 is formed with passages 23 and 25 which accommodate the inlet and outlet means 15 and 16 of the sac. A second housing 27 is seated between the passages 23 and 25 and contains the displacing means 19. The second housing is provided with a pair of extensions 29 and 31 which house the arms of the displacing means described in detail below.

Figure 3:
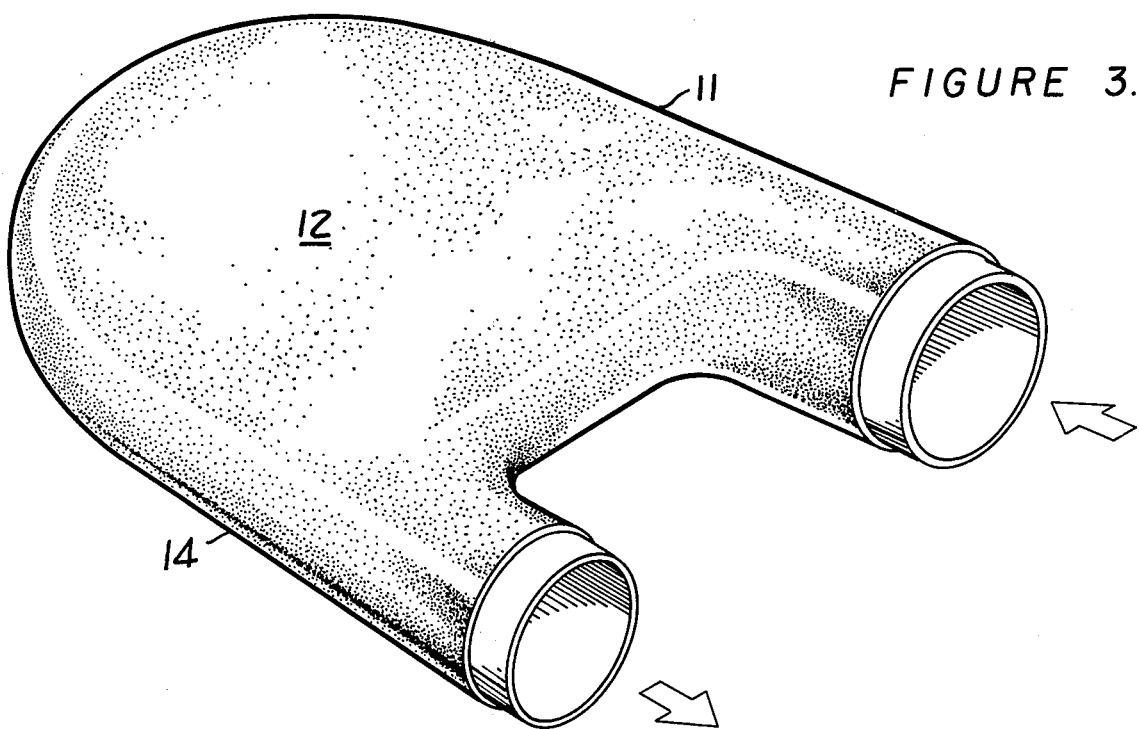
FIG. 3 is a isometric view illustrating the sac geometry of the device of the invention when the sac is in the nondeformed configuration.
Figure 4:
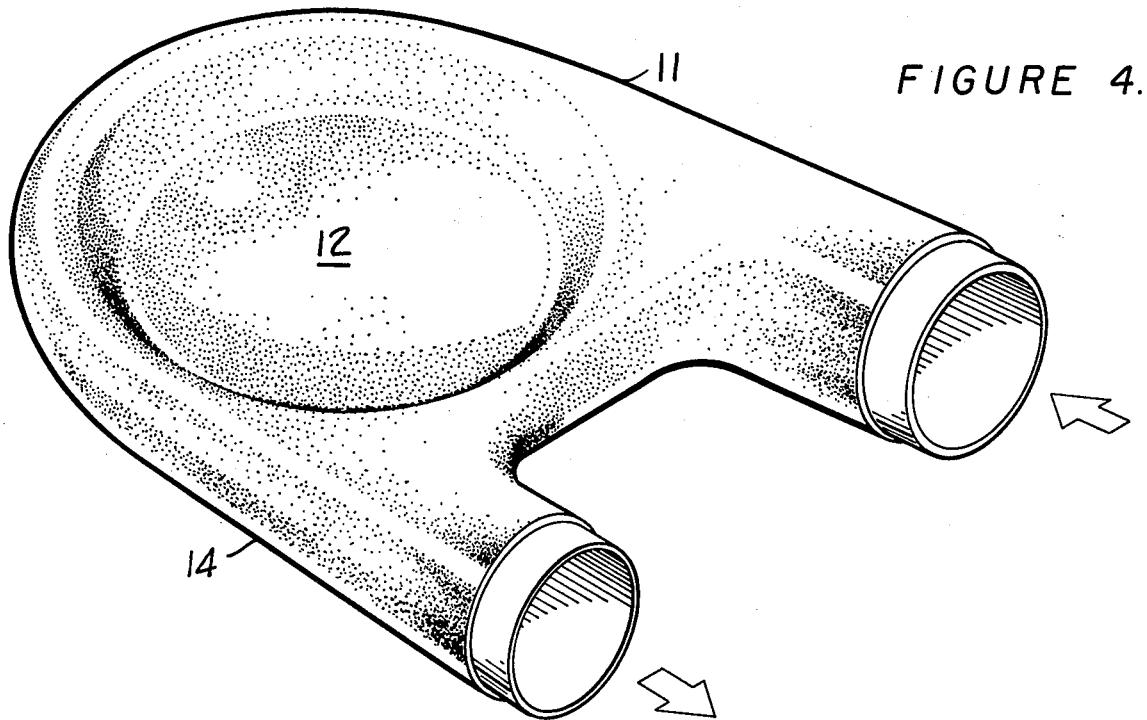
FIG. 4 is an isometric view of the sac of the device of the invention in the deformed configuration.

The sac itself may be more clearly seen in FIGS. 3 and 4 which are isometric views of the sac showing it in the nondeformed configuration and the deformed configuration, respectively. The sac is formed in a unitary seamless piece of flexible resilient, blood compatible, material. This material may be of any type suitable for pumping blood such as certain types of polyurethanes. The material of which the sac is comprised should have long-term retention of physical strength under combined dynamic stressing and hydrolysis. The material should be of low toxicity and long-term chemical stability for compatibility with blood. The material should also be of high strength, be capable of being repeatedly flexed, be capable of being sterilized, and be easily fabricated. Suitable materials are linear segmented polyurethanes, for example, BIOMER from Ethicon.

The internal surface of the sac should be selected to avoid thrombus formation. Two types of blood contacting surfaces which may be satisfactory are textured surfaces which encourage pseudointimal growth and smooth polyurethane antithrombogenic surfaces.

The inlet and outlet means 15 and 16 are illustrated as a pair of conduits which are formed in a unitary piece with the sac 11. The conduits are of generally circular cross-section and extend tangentially of the annulus formed by the annular wall 14 of the sac. This is for the purpose of directing the blood flow tangentially into the interior of the sac and out of the interior of the sac to thereby minimize discontinuities in the flow and reduce the likelihood of thrombus formation.

The inlet means is made of slightly expanding diameter inwardly or with an expanding taper in order to direct a portion of the incoming blood toward the center of the sac and thus avoid the formation of a vortex in the center of the sac which might additionally contribute to thrombus formation. This configuration also helps to reduce flow separation at the junction between the inlet conduit and the main portion of the sac. If there is too sudden an expansion of inflow in this area, adverse pressure gradients will be established near the walls of the sac resulting in flow separation and in a region of stasis. The outlet conduit is also designed with a smooth transition from the main sac body to the outlet conduit. In order to assure a low pressure drop, the inflow section should be made as short and as large in diameter as possible. The gradually expanding transition section mentioned above is helpful in this respect.

The two pusher plates 17 and 18, disposed on opposite sides of the sac, operate to deform the sac for the outflow stroke and then move back in order to allow the sac to expand to its normal nondeformed configuration. By utilizing dual pusher plates, a good washing of all internal surfaces of the sac occurs to prevent the formation of stagnation zones leading to thrombus formation. Moreover, because of the generally symmetrical shape of the sac, the collapse or deformation of the sac is symmetrical, resulting in good blood flow patterns with minimal stagnation zones. This is particularly true at the transition zones of the sac at the inflow and outflow conduits.

Referring to FIG. 4, the deformed condition of the sac may be seen. It will be observed that a gentle low profile rolling deformation occurs in the semicircular cross-section annular wall 14, and that low strain deformation occurs at the transition areas between the main sac and the inlet and outlet conduits. Moreover, the likelihood of the formation of wrinkles is minimized, thereby maintaining smooth surfaces for the blood flow. Moreover, the use of dual pusher plates reduces the total overall stroke required, producing gentle deformation and reducing the likelihood of wrinkling. The severity of the wrinkling problem increases with stroke length.

Suitable valves, not shown, are provided in the inlet and outlet conduits 15 and 16, respectively, to provide the desired pumping action. Several xenograft valves are available on the market and such may be suitable. For example, Hancock Corporation's Porcine xenograft prostheses appears to be a suitable valve for this purpose. Xenograft valves typically have low regurgitation and leakage problems, lower opening and closing times, and better flow profiles.

For the purpose of producing the deformation of the sac previously described and illustrated in connection with FIGS. 3 and 4, the pusher plates 17 are actuated by the displacing means 19. The displacing means are contained in the second housing 27 and its extensions 29 and 31. The displacing means may comprise a solenoid actuator 33 which is of high efficiency, electronically controlled, and pulsed. Use of a solenoid having an armature which is decoupled from the blood pump mechanical drive by means of an intermediate energy storage spring provides high efficiency, low inertia, and high responsiveness at cardiac rates. Moreover, the inherent simplicity of a solenoid drive offers long term reliability. Such a solenoid drive is available from the Andros Corporation, Berkeley, Calif., under the designation MK19 and MK20.

The actuator is illustrated specifically at 33 in FIG. 1 and is coupled to a pair of arms 39 and 41 (FIG. 2) which are mounted at pivots 43. The opposite ends of the arms 39 and 41 from the actuator 33 are coupled by suitable linkages 47 and 49, respectively, to the pusher plates 17 and 18. Thus, energization of the actuator 33 moves the arms simultaneously to displace the plates periodically toward each other and back to the expanded contion. This is shown in dotted lines in FIG. 2.

For use as a left ventricular assist device, the illustrated blood pump may be designed with a total pump volume including inflow and outflow conduits of 28 milliliters and with a total mass of approximately 150 grams. The pump may be designed for a stroke volume of 85 milliliters, with each pusher plate having a maximum stroke of 9.6 millimeters. Under such conditions, the inflow and outflow sections may be designed to accommodate 29 millimeter valves, respectively.

It may be seen, therefore, that the invention provides an improved blood pumping device for internal use in humans or animals and which is particularly suited for use as a left ventricular assist device. By utilizing dual pusher plates, pusher plate stroke and consequently sac deformation may be reduced by a factor of two. The shape of the sac and the single unitary seamless construction thereof results in smooth transition areas on internal surfaces, minimizing stress and wrinkling. Moreover, sites for thrombus formation are minimized and a smooth circular flow with even washing of all pump surfaces results.

Various modifications of the invention will become apparent to those skilled in the art from the foregoing description and accompanying drawings. Such modifications are intended to fall within the scope of the appended claims.

What is claimed is:

1. A blood pumping device for internal use in humans or animals and comprising, a deformable sac having in the nondeformed configuration a pair of opposite substantially parallel and planar walls of substantially circular shape joined by an annular wall of substantially semicircular cross-section, said sac being formed in a unitary seamless piece of flexible resilient material and having inlet and outlet means in said annular wall, a pair of plates disposed on opposite sides of said sac, each of said plates being engageable with a respective one of said planar walls of said sac for displacing said planar walls toward each other to deform said sac, and means for periodically displacing both of said plates simultaneously toward each other.

2. A device according to claim 1 wherein said inlet and outlet means comprise conduit means arranged to direct inlet and outlet flow substantially tangentially with respect to the annulus defined by the inner surface of said annular wall.

3. A device according to claim 2 wherein said inlet means are formed so as to direct a portion of the inlet flow toward the center of said sac.

4. A device according to claim 1 wherein said displacing means comprise electrically actuated solenoid means.

5. A blood pumping device for internal use in humans or animals and comprising, a deformable sac having in the nondeformed configuration a pair of opposite substantially parallel and planar walls of substantially circular shape joined by an annular wall of substantially semicircular cross-section, an inlet conduit and an outlet conduit of substantially circular cross-section extending from said annular wall of said sac substantially tangentially with respect to the annulus defined by said annular wall, said sac and said inlet and outlet conduits being formed in a unitary seamless piece of flexible resilient material, a pair of plates disposed on opposite sides of said sac, each of said plates being engageable with respect to one of said planar walls of said sac for displacing said planar walls toward each other to deform said sac, and means for periodically displacing said plates toward each other.

6. The device of claim 5 including valve means disposed in said inlet and outlet conduits.

7. A device of claim 5 wherein said inlet conduit is formed with a diverging diameter so as to direct a portion of the inlet flow toward the center of said sac.

8. A device according to claim 5 wherein said inlet and outlet conduits extend from the same side of a diameter of said annular wall so as to form a space therebetween, and wherein said displacing means are arranged in said space.

* * * * *